US00PP22791P2

(12) United States Plant Patent
Saul

(10) Patent No.: US PP22,791 P2
(45) Date of Patent: Jun. 12, 2012

(54) ***KNIPHOFIA* PLANT NAMED 'ECHO ROJO'**

(50) Latin Name: *Kniphofia uvaria*
Varietal Denomination: Echo Rojo

(75) Inventor: Richard G. Saul, Cleveland, GA (US)

(73) Assignee: Itsaul Plants, LLC, Alpharetta, GA (US)

( * ) Notice: Subject to any disclaimer, the term of this patent is extended or adjusted under 35 U.S.C. 154(b) by 314 days.

(21) Appl. No.: 12/661,875

(22) Filed: Mar. 25, 2010

(51) Int. Cl.
*A01H 5/00* (2006.01)

(52) U.S. Cl. ..... Plt./443

(58) Field of Classification Search ..... Plt./443
See application file for complete search history.

(56) References Cited

U.S. PATENT DOCUMENTS

| | | | | |
|---|---|---|---|---|
| PP12,342 | P2 * | 1/2002 | Trujillo | Plt./258 |
| PP21,706 | P2 * | 2/2011 | Saul | Plt./443 |
| PP21,905 | P2 * | 5/2011 | Schreurs | Plt./443 |

* cited by examiner

*Primary Examiner* — Wendy C Haas
(74) *Attorney, Agent, or Firm* — Penny J. Aguirre

(57) ABSTRACT

A new cultivar of *Kniphofia*, 'Echo Rojo', characterized by its inflorescences that start orange in color and turn red as they mature, its early blooming habit with the first blooms appearing at the end of April to the first part of May in Georgia, its repeat bloom throughout the summer, its semi-evergreen foliage that remains clean, and its strong upright stems that reach 36 inches in height and do not lodge.

2 Drawing Sheets

Botanical classification: *Kniphofia uvaria.*
Varietal denomination: 'Echo Rojo'.

CROSS REFERENCE TO A RELATED APPLICATION

This application is co-pending with a U.S. Plant Patent Application filed for a plant derived from the Inventor's breeding program that is entitled *Kniphofia* Plant Named 'Echo Mango' (U.S. Plant Pat. No. 21,706.

BACKGROUND OF THE INVENTION

The present invention relates to a new and distinct cultivar of *Kniphophia uvularia* and will be referred to hereafter by its cultivar name, 'Echo Rojo'. 'Echo Rojo' is a new cultivar of red hot poker or torch lily, a perennial grown for landscape use.

The new cultivar was derived from a controlled breeding program conducted by the Inventor at his nursery in Dahlonega, Ga. The overall purpose of the breeding program is to make selections of *Kniphofia* with unique flower colors combined with a reblooming habit and strong stems. 'Echo Rojo' was selected in the Inventor's trial bed in June 2007 as a single unique plant from amongst the seedlings derived from a cross made in April 2006 between 'Firelight' (not patented) as the female parent and 'Candlelight' (U.S. Plant Pat. No. 12,342) as the male parent.

Asexual reproduction of the new cultivar was first accomplished by division by the Inventor in Dahlonega, Ga. in June of 2007. The characteristics of this cultivar have been determined both by division and in vitro propagation to be stable and to reproduce true to type in successive generations.

SUMMARY OF THE INVENTION

The following traits have been repeatedly observed and represent the characteristics of the new cultivar of *Kniphofia*.

These attributes in combination distinguish 'Echo Rojo' from all other selections of *Kniphofia* known to the Inventor.

1. 'Echo Rojo' exhibits an early blooming habit with the first blooms appearing at the end of April to the first part of May in Georgia.
2. 'Echo Rojo' exhibits a long blooming period than is typical of the species, producing blooms until fall.
3. 'Echo Rojo' exhibits a reblooming habit with several blooms throughout the summer.
4. 'Echo Rojo' exhibits semi-evergreen foliage that remains cleaner than is typical of the species.
5. 'Echo Rojo' exhibits a clump-forming habit with strong upright stems that do not lodge.
6. 'Echo Rojo' reaches a height of 94.1 cm (36 inches).
7. 'Echo Rojo' exhibits inflorescences that are dark orange as they start to bloom and turn red as they mature.

'Echo Rojo' can be distinguished from its parent plants. The female parent, 'Firelight' differs from 'Echo Rojo' in being 15 cm (6 inches) shorter in height, in having a habit that tends to flop, and in having flowers that are uniformly red throughout the blooming period. The male parent, 'Candlelight', differs from 'Echo Rojo' in being 30 cm (12 inches) shorter in height, in having a habit that tends to flop, and in having yellow flowers. 'Echo Rojo' can be distinguished from the species, *Kniphofia uvaria*, in having a reblooming habit, earlier blooming, a longer blooming period and stems that remain upright. 'Echo Rojo' can also be compared to the cultivar 'Nancy's Red' (not patented). 'Nancy's Red' is similar to 'Echo Rojo' in its blooming habit and grassy foliage but differs from 'Echo Rojo' in lacking a reblooming habit, in being shorter in height, and in having inflorescences that are uniformly red. 'Echo Rojo' can also be compared to the cultivar 'Echo Mango'. 'Echo Mango' is similar to 'Echo Rojo' in its early blooming habit but differs from 'Echo Rojo' in being taller in height and in having inflorescences that are apricot in color.

BRIEF DESCRIPTION OF THE DRAWING

The accompanying colored photographs illustrate the overall appearance and distinct characteristics of the new *Kniphofia*. The photographs were taken of 2 year-old plants as grown in a garden in Atlanta, Ga.

The photograph in FIG. 1 illustrates the overall habit and appearance of two plants of 'Echo Rojo' in bloom.

Figure 1:
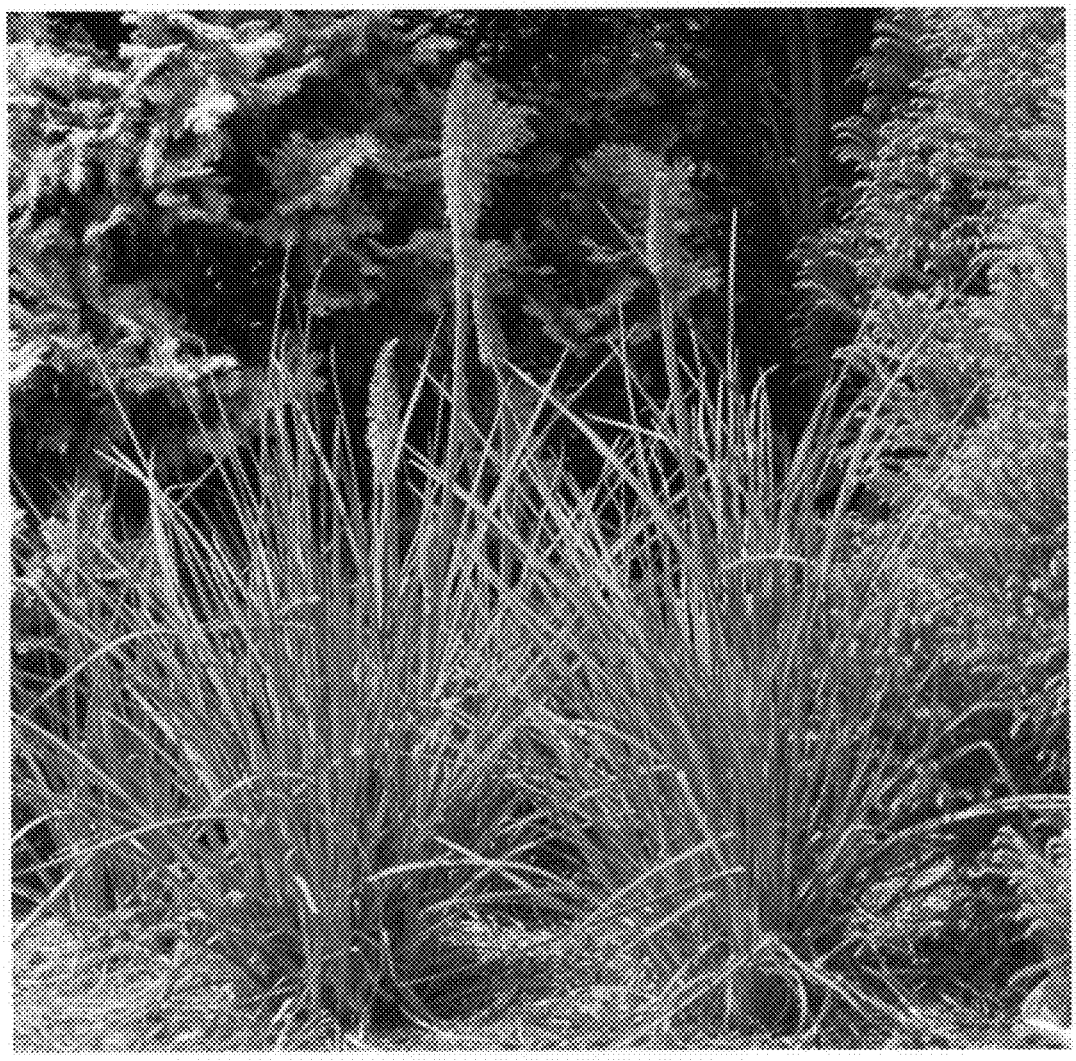
Figure 2:
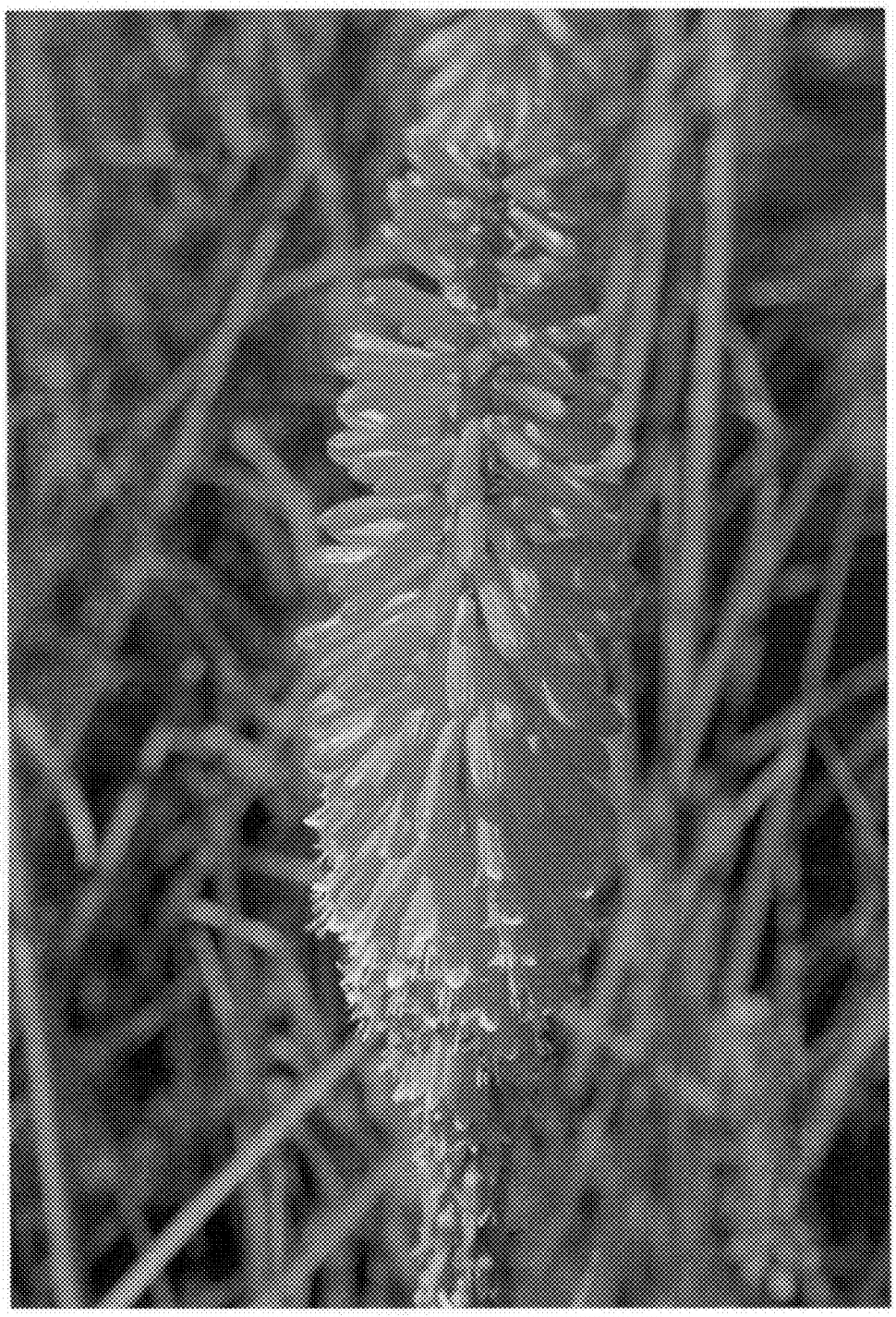

The photograph in FIG. 2 provides a close-up view of an inflorescence of 'Echo Rojo'. The colors in the photograph may differ slightly from the color values cited in the detailed botanical description, which accurately describe the colors of the new *Kniphofia*.

DETAILED BOTANICAL DESCRIPTION

The detailed botanical data describes one-year old plants of 'Echo Rojo' as grown in one-gallon containers in a greenhouse in Dahlonega, Ga. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming habit*.—Blooms in April and then repeated throughout the summer.

*Plant type*.—Semi-evergreen perennial.

*Plant habit*.—Upright with foliage slightly cascading but without lodging, clump-forming basal grass-like leaves with upright flowers stems emerging from center of each division.

*Height and spread*.—About 91.4 cm (36 inches) in height in bloom and 61 cm (24 inches) in spread.

*Hardiness*.—U.S.D.A. Zones 6 to 9.

*Diseases and pests*.—No unique aspects concerning susceptibility or resistance to diseases or pests has been observed.

*Environmental stresses*.—Semi-evergreen foliage remains clean (cleaner than is typical of the species).

*Root description*.—Fleshy and thick.

Growth and propagation:

*Propagation*.—Tissue culture or division.

*Time required for root development*.—A 2-inch plug can be finished in about 5 to 6 weeks at 25° C. in summer (6 to 7 weeks in winter) from a division, and in about 6 weeks at 27° C. in summer (8 weeks in winter) when produced by tissue culture.

*Growth rate*.—Vigorous.

Foliage description:

*Leaf shape*.—Linear.

*Leaf division*.—Simple.

*Leaf base*.—Truncate and sheathed to base of shoot.

*Leaf apex*.—Narrowly acuminate.

*Leaf aspect*.—Sulcate, leaves initially emerge upright, then upright to slightly cascading.

*Leaf venation*.—Parallel, the midrib is raised on the lower surface, not prominent or conspicuous, color matches leaf color.

*Leaf margins*.—Entire, scabrous.

*Leaf attachment and arrangement*.—Sessile, rosette-like.

*Leaf size*.—Average of 1.2 cm in width (at midpoint) and an average of 60 cm in length when mature.

*Leaf number*.—Average of 16 per rootstock (shoot).

*Leaf surface*.—Glabrous and glandular on upper and lower surface.

*Leaf color*.—Newly emerging leaves upper and lower surfaces: 137B, mature leaves upper and lower surface; 137B becoming a blend of 144A and 145A near base.

Flower description:

*Inflorescence type*.—Dense racemes of single flowers held on erect and strong scapes.

*Inflorescence size*.—Reaches up to 11 cm in height and about 4.5 cm in width.

*Flower fragrance*.—None.

*Flower quantity*.—An average of 135 flowers per raceme.

*Flower lastingness*.—Flowers open from base towards the apex, average of 5 days per flower, not persistent.

*Flower buds*.—Oblong-obovate in shape, between 4 to 6 mm in diameter and 1 to 2 cm in length, emerge 34B in color and mature to 31A blended to 23C towards base.

*Flower aspect*.—Held horizontally then slightly downward at about a 15° angle to the stem as they mature.

*Flower shape*.—Tubular.

*Flower size*.—About 3 cm in depth and 8 mm in diameter.

*Tepals*.—6 (rarely 5), about 2 cm in length and fused into tube with triangular-shaped free apex; about 4 mm in width and 3 mm in length, margin is entire, apex is broadly acute, upper and lower surface is glabrous and waxy, color when fully open on outer and inner surface; a blend of 31A and 23C with prominent mid rib 39A, color fades to a blend of 32B and 32C.

*Peduncles* (*scapes*).—About 70 cm in length (from base of plant to top of raceme) and an average of 1 cm in width, held erect, very strong, color is 144A, surface is glabrous and waxy.

*Pedicels*.—Average of 2 mm in length and 1 mm in width, 152A in color, surface is glabrous and waxy.

Reproductive organs:

*Gynoecium*.—1 Pistil, about 2.3 cm in length, stigma is crested, minute and 11C in color, style is about 2.3 cm in length and 11B in color, ovary is superior, globose in shape, about 2 cm in length and width and 13A in color.

*Androcoecium*.—6 stamens, anthers are oblong in shape, dorsifixed, about 1.5 mm in length and 1 mm width and 13B color, filaments are about 2.8 cm in length a blend of 1C and 8C in color, pollen is low in quantity and 12A in color.

*Fruit and seed*.—Capsules; produced more abundantly when grown outdoors, ovoid-globose in shape, 3-parted, about 9 mm in length and 8 mm in width, a blend of 144A and 147A in color maturing to a blend of N200A, N200B, and 199A on the outer surface and 199B on the inner surface, glaucous surface becoming woody when mature, seeds; 3 per capsule, 3.5 to 4 mm in length, 200A in color.

It is claimed:

1. A new and distinct cultivar of *Kniphofia* plant named 'Echo Rojo' as herein illustrated and described.

* * * * *